United States Patent [19]

Gross

[11] Patent Number: 4,852,563

[45] Date of Patent: Aug. 1, 1989

[54] MULTIFUNCTION CONNECTOR FOR A BREATHING CIRCUIT

[75] Inventor: James R. Gross, St. Charles, Ill.

[73] Assignee: The Kendall Company, Boston, Mass.

[21] Appl. No.: 65,203

[22] Filed: Jun. 22, 1987

[51] Int. Cl.[4] ............................................. A62B 9/04
[52] U.S. Cl. ....................... 128/202.27; 128/204.18; 128/912; 128/719; 128/736; 285/179; 285/305; 285/275
[58] Field of Search .............. 128/202.27, 204.18, 128/912, 719, 736, 716, 724; 604/283, 289; 285/179, 305, 308, 311, 319, 320, 921, 275

[56] References Cited

U.S. PATENT DOCUMENTS

| | | | |
|---|---|---|---|
| 3,461,877 | 8/1969 | Morch | 285/272 |
| 4,214,728 | 7/1980 | Fleischer | 285/320 |
| 4,270,778 | 6/1981 | Brownell | 604/283 |
| 4,326,516 | 4/1982 | Schultz et al. | 604/283 |
| 4,385,629 | 5/1983 | Wolf, Jr. et al. | 128/912 |
| 4,409,163 | 9/1983 | Voges et al. | 285/505 |
| 4,413,632 | 11/1983 | Schlossinger et al. | 128/716 |
| 4,506,665 | 3/1985 | Andrews et al. | 128/912 |
| 4,557,261 | 12/1985 | Rugheimer | 604/283 |
| 4,589,684 | 5/1986 | Nowacki et al. | 285/319 |
| 4,612,929 | 9/1986 | Schubert et al. | 128/912 |
| 4,621,634 | 11/1986 | Nowacki et al. | 804/283 |
| 4,648,658 | 8/1972 | Gross | 604/283 |
| 4,673,200 | 6/1987 | Miyauchi | 285/319 |
| 4,677,987 | 7/1987 | Choksi | 128/719 |
| 4,747,621 | 5/1988 | Gans et al. | 285/275 |
| 4,756,670 | 7/1988 | Arai | 128/719 |
| 4,770,445 | 9/1988 | Steer et al. | 285/319 |
| 4,774,940 | 10/1988 | Linder | 128/912 |
| 4,787,655 | 11/1988 | Gross et al. | 128/207.16 |

FOREIGN PATENT DOCUMENTS

| | | | |
|---|---|---|---|
| 2805416 | 9/1978 | Fed. Rep. of Germany | 285/319 |
| 1195896 | 3/1969 | United Kingdom | 285/319 |

Primary Examiner—Max Hindenburg
Assistant Examiner—K. M. Reichle
Attorney, Agent, or Firm—Alvin Isaacs

[57] ABSTRACT

A component of a breathing circuit for directing air to a patient requiring treatment. The component comprises a tubular conduit having a male end and a female end. A locking clip is disposed on the housing adjacent the male end of the component. A plurality of annular rings are disposed on the outer side of the female end. The annular rings are engagable by a locking clip of an adjacent component. A sampling port is disposed through the housing to permit sampling of the air within the breathing circuit.

4 Claims, 1 Drawing Sheet

MULTIFUNCTION CONNECTOR FOR A BREATHING CIRCUIT

BACKGROUND OF THE INVENTION

(1) Field of the Invention

This invention relates to breathing circuits, and more particularly to connective members within those breathing circuits.

PRIOR ART

Breathing Circuit components usually are arranged to mate with one another through friction-fitted interconnections. Serious injuries with anesthesia patients occur rarely, but serious injury and some deaths do occasionally happen during surgical procedures, due to accidental disconnections in the breathing circuit components. In these components it is desirable, to not only have them readily lockable together, but to have sampling means therein, so as to determine the nature of the fluid passing through the component. It is particularly desirable to have the locking arrangement as part of a sampling port in a breathing circuit component, because that particular component is the one which would be the most likely to be turned or manipulated and thus most likely to be accidentally disconnected.

A recent patent issued to Schubert et al, U.S. Pat. No. 4,612,929 shows a swivel elbow having a sampling port thereon. Parts are held together by snap rings. This type of assembly is an improvement over some of the art, but it doesn't provide the backup systems that are sometimes necessary to prevent failure.

An example of the friction-fit intermating between elements of a breathing circuit, is shown in U.S. Pat. No. 4,521,038 to Cerny. The backup locking connection with a sampling port is just not shown. A fairly complicated arrangement is shown in U.S. Pat. 4,637,384 to Schroeder, wherein an overlapping arrangement of components are arranged to fit snugly together.

A further connection which adapts with a locking device is shown in U.S. Pat. No. 4,214,728 to Fleischer which shows a spring loaded coupling arranged with a friction-fit. A further example of the art wherein friction mating components are shown, is represented by U.S. Pat. No. 4,506,665 to Andrews et al. This is merely a friction-fitting between the components and it does not show a sampling port therewith. U.S. Pat. No. 4,557,261 to Rugheimer, shows a spring-loaded outer arm for interlocking mating components of a breathing circuit together. This patent however does not show a sampling port nor does it shows a backup system for locking the components together should the first portion of the locking arrangement slip. U.S. Pat. No. 4,621,634 to Nowacki et al does show a simplistic locking arrangement on a portion of its components but they fail to follow through having the locking means on each end of its components, and they do not include the tapered male and female end portions to permit fitting with "standard" connectors.

BRIEF SUMMARY OF THE INVENTION

The present invention relates to an element utilized in a breathing circuit, which element may be adapted to lock certain other components of that circuit together. The present component also is adapted to provide sampling capabilities into that breathing circuit. The circuit component has frictional-fit capabilities at both ends of its tubular structure. There are also locking arrangements disposed at each end thereof. The sampling means is disposed between the two ends of the circuit component. The circuit component may be an elbow shaped structure or it may be a linear structure. The circuit component on one end thereof comprises a male means, having a locking clip extending adjacent the male end, and having a lifting tab on the distal end of the locking clip. The female end of the circuit component has a plurality of annular rings disposed in a spaced apart fashion from the end thereof. The male end of the elbow component may for example mate frictionally with the female end of a wye component which provides a conduit means from gaseous sources. There are at least two annular rings axially spaced apart from one another on the female end of the connector component.

In the normal mating of the components comprising a circuit, the locking clip would go over the second inwardly innermost or proximalmost annular ring. The annularity of the ring and the annular sliding relationship of the locking clip around the second ring permits the circuit components to be rotated with respect to one another. This is critically significant, because the sampling port may not be oriented particularly accurately when the element is assembled in the breathing circuit and it would have to be rotated, while it is in place in the breathing circuit. The locking clip may become loosened during this rotation by the medical personnel, or the patient but the first or distalmost annular ring around the female end of the circuit element is disposed so as to provide the last lip (ring) to catch the end of the locking clip thereon. This concept is utilized whether the circuit component is an elbow member or a linear or straight member.

It is an object of the present invention, to provide a circuit component having the capability of mating on a frictional basis with other standard sized circuit components which may not have the locking elements therewith.

It is a further object of the present invention, to provide a circuit component which has a backup locking means which will permit angular adjustment of the components with respect to one another, yet provide a second locking means should the first interlocking arrangement slip.

It is yet a further object of the present to permit a sampling means within the circuit component itself, particularly on a circuit component which is critical to the sampling needs of the breathing circuit, and which component would be the most likely to become disattached from the circuit to which it is connected.

BRIEF DESCRIPTION OF THE DRAWINGS

The objects and advantages of the present invention will become more apparent, when viewed in conjunction with the drawings, in which.

DESCRIPTION OF THE PREFERRED EMBODIMENTS

Figure 1:
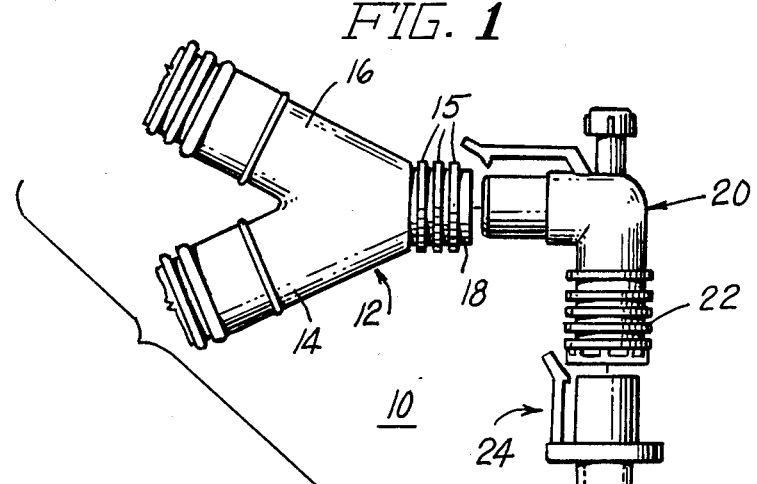
FIG. 1 is a plan view of a portion of a breathing circuit showing several components thereof.

Referring now the drawings in detail, and particularly to FIG. 1, there is shown a portion of a gaseous fluid conducting breathing circuit 10. The breathing circuit 10 may comprise a wye 12 having a pair of legs 14 and 16 which extend to a pressurized gas source, not shown, the wye 12 having a female end 18 which mates with an elbow member 20. The wye 12 has a plurality of annular rings 15 axially spaced along its female end 18. The elbow member 20 has a female end 22 which mates with an endotracheal tube adapter 24. The endotracheal tube adapter 24 mates with an endotracheal tube 26 which is receivable in a patient's throat.

Figure 2:
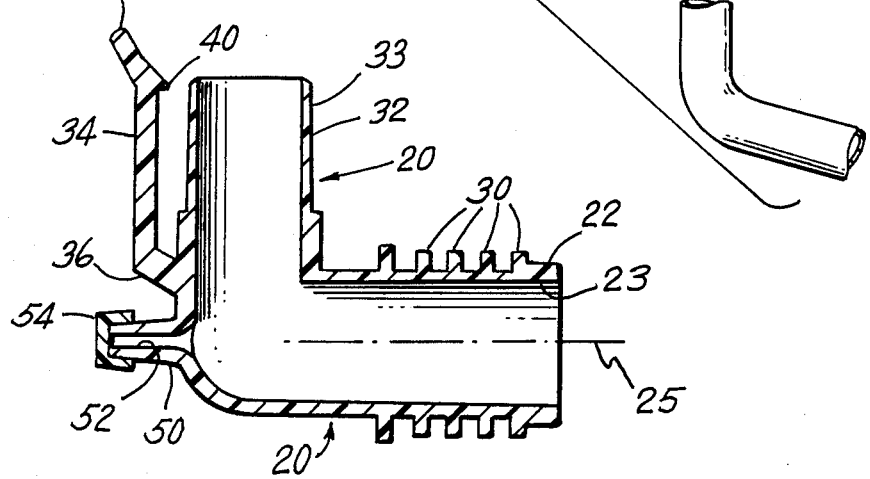
FIG. 2 is a side elevational view of an elbow component of that breathing circuit.

The elbow member 20 is shown more particularly in FIG. 2. The elbow 20 is a hollow conduit structure having a generally 90° bend in its housing near its midpoint. The female end 22 of the elbow 2 has at least two annular rings 30 (four are shown), spaced longitudinally from one another but are coaxially arranged. The opening comprising the female end 22 has an opening surface 23 with a slight taper with respect to its axis 25. The elbow has a male end 32 which has an outer surface 23 with a slight taper. A locking clip 34 is disposed parallel to the longitudinal axis 25 of the male end 32 of the elbow 20. The locking clip 34 has a proximal end 36 at which it is attached to the elbow 20 adjacent its midpoint. The locking clip 34 has a tab 38 on its distal end which extends at an angle away from the longitudinal axis 25 of the male end 32 of the elbow 20. The tab 38 is utilized for lifting purposes to permit manual bending the locking clip 34. An engaging tooth 40, directed radially inwardly, is disposed adjacent the tab 38. The tooth 40 is utilized to engage the proximal side of the annular rings on any mating component which may have them, such as those rings 15 that shown on the wye 12 in FIG. 1. It is significant that the annular rings 30 number at least two on the female end of the particular circuit member on which they are located. In that way the tooth 40 will engage the proximal side of the annular ring 30 which is furthermost from the end of the element. Thus if the locking clip 34 were somehow loosened when the elbow 20 is rotated in place in the breathing circuit 10, so as to slip a bit from its adjacent component it would slip back only to the next adjacent annular ring distal from the previous ring 30. Thus a backup is shown and may be very necessary when a particular circuit element is turned in a breathing circuit. The elbow 20 in this embodiment also has a sample port 50 attached to the housing of the elbow 20. The sample port 50 has a hollow cylindrical center portion 52 which is in fluid communication with the channel portion of the elbow 20. The sample port 50 has a cap 54 which is engagable about the distal end of the sample port 50 to seal it when not in use. The locking clips are particularly critical on both ends of a circuit component such as shown in FIGS. 1 and 2, because when an anesthesiologist has to take a sample of the air within the circuit 10, that particular component may have to be rotated so as to align the sample port 50 with the sampling mechanism. A mere frictional engagement between the components of the breathing circuit may otherwise permit a break in that circuit to occur with very possible harmful effects to the patient.

Figure 3:
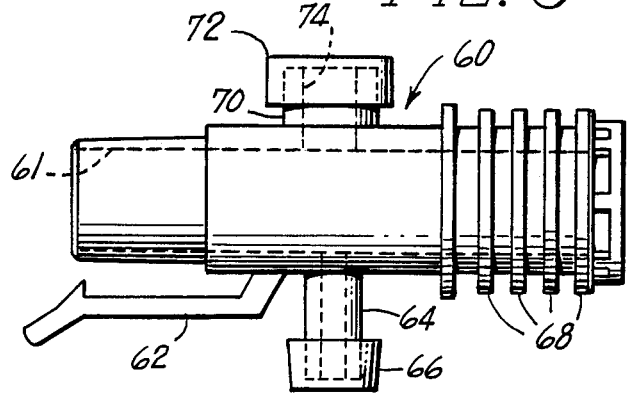
FIG. 3 is a view of a breathing circuit component of a linear nature.

A similar circuit component is shown in FIG. 3, wherein a circuit component 60 is shown comprising a tubular member of linear configuration having a central conduit 61. The linear circuit component 60 has a locking clip 62 as described in the aforementioned embodiment shown in FIG. 2. The linear breathing circuit component 60 has a sampling port 64 extending into the hub of the component 60. The sampling port 64 has a cap 66 which mates over the top of the port so as to keep it sealed when the sampling port 64 is not in use. The linear component 60 also has a temperature sampling port 70 with a removable cap 72 thereon. The sampling port 70 has a central channel 74 which is in fluid communication with the central conduit 61. The temperature sampling port 70 permits simultaneous temperature sensing while testing the air therethrough. The linear component 60 has a plurality (more than two) of annular rings 68 in a spaced apart relationship about the female end of the element 60.

Thus there has been shown a breathing circuit system wherein a plurality of elements making up that system each have a mating array of lockable elements on each end thereof. Each lockable element alternates with respect to the particular end in that particular part of the system. Each component of the present invention will function satisfactorily with a nonlockable element of a component from a nonlockable system. That is to say even if the locking elements are not in use, the components will still frictionally engage one another in a manner that is common in the art because of their standard tapers. The present invention however includes the multiple safety backup locking arrangement permitting articulation of the particular components as well as a sampling port within any particular component which itself however necessitates the articulation of that component within the system.

I claim:

1. A component which is part of and articulatable with respect to a breathing circuit for directing the flow of air to and from a patient, while permitting the safe sampling of air from therewithin, the breathing circuit including a first component having a female end including at least two annular rings as part of the outer surface thereof and a second component having a male end and locking clip means adjacent thereto the component comprising:

a hollow housing having a first male end and a second female end, said male end having a tapered outer surface means for frictional engagement and communication with the female end of the first component in the breathing circuit, said female end having a tapered inner receiving surface means for frictional engagement and communication with the male end of the second component in the breathing circuit;

an air sampling port disposed on said component housing and in fluid communication with said hollow housing therewithin;

locking clip means arranged on said housing adjacent the male end of said component for engaging any one of the rings on the first component to allow articulation therebetween means for receiving the locking clip means of the second component to allow articulation therebetween, disposed about the female end of said component, said locking clip receiving means comprising a plurality of annular rings as part of the outer surface of said female end of said component.

2. An articulatable component of a breathing circuit as recited in claim 1, wherein said housing of said component has a bend therein, so as to comprise an elbow.

3. An articulatable component of a breathing circuit as recited in claim 1, wherein said locking clip means has a tab directed radially inwardly thereon, so as to permit it to overlap an annular ring on the first component mating therewith.

4. An articulatable component of a breathing circuit, as recited in claim 1, including a temperature sensing port to permit simultaneous temperature monitoring with the air quality sensing through the air sampling port.

* * * * *